United States Patent [19]

Bimman

[11] Patent Number: 5,334,184
[45] Date of Patent: Aug. 2, 1994

[54] APPARATUS FOR INTRAMEDULLARY FIXATION BROKEN BONES

[76] Inventor: Lev A. Bimman, 100 N. La Cumbre Rd., Apt. 18, Santa Barbara, Calif. 93110

[21] Appl. No.: 906,385

[22] Filed: Jun. 30, 1992

[51] Int. Cl.$^5$ ............................ A61F 5/04; A61F 2/28
[52] U.S. Cl. ......................................... 606/63; 623/16
[58] Field of Search ...................... 606/60, 61, 62, 63; 623/16, 18, 23

[56] References Cited

U.S. PATENT DOCUMENTS

| | | | |
|---|---|---|---|
| 4,016,874 | 4/1977 | Maffei et al. | 606/62 |
| 4,590,930 | 5/1986 | Kurth et al. | 606/63 |
| 4,888,024 | 12/1989 | Powlan | 623/23 |
| 4,932,975 | 6/1990 | Main et al. | 623/17 |
| 5,059,193 | 10/1991 | Kuslich | 606/61 |
| 5,060,635 | 10/1991 | Steur et al. | 623/17 |
| 5,074,882 | 12/1991 | Grammont et al. | 623/23 |
| 5,092,891 | 3/1992 | Kummer et al. | 606/62 |
| 5,102,413 | 4/1992 | Poddar | 606/63 |

FOREIGN PATENT DOCUMENTS

| | | | |
|---|---|---|---|
| 0662082 | 5/1979 | U.S.S.R. | 606/63 |
| 1109142 | 8/1984 | U.S.S.R. | 606/63 |

*Primary Examiner*—David Isabella
*Attorney, Agent, or Firm*—Streck & Wallage

[57] ABSTRACT

An apparatus comprising an internal bone fixation apparatus for supporting and securing together two sections of a fractured elongated bone within a patient's body. Generally, the apparatus includes first and second fixation portions which are disposed in holes formed in the internal cavity of the fractured bone on respective sides of the fracture, and a means for connecting these fixation portions together. In the preferred version of the present invention, the connecting means is adjustable such that the first and second fixations portions can be drawn together or spread apart in the longitudinal direction, thereby similarly moving the first and second sections of the fractured bone. In addition, the structural and securing portions of the invention are made from strong resilient metals, that are not necessarily compatible for long term contact with the body of the patient. However, the metals are completely isolated from any contact with the body of the patient by insulating materials which are compatible.

12 Claims, 1 Drawing Sheet

APPARATUS FOR INTRAMEDULLARY FIXATION BROKEN BONES

BACKGROUND OF THE INVENTION

1. Technical Field

The present invention is directed, in general, to devices for orthopedic surgery, and more particularly to an apparatus for the internal fixation of an elongated broken bone.

2. Background Art

Prior art methods in the field of orthopedic surgery employed to secure and align fragments of a broken bone during the healing process traditionally involve the use of metal screws, pins, nails, wire, and the like. Metal plates are also sometimes screwed to the outside of the bone to secure the bone fragments. These traditional devices are often difficult and time consuming to install. This results in the patient being in surgery for extended periods of time, thereby increasing the risks inherent with surgery in general. In addition, these methods merely secure and align the bone fragments together while they mend.

However, some types of fractures require more than merely securing and aligning the bone fragments. In the case of elderly patients, the bone may not be capable of properly mending. In bone injuries where the fracture site is severely shattered there can be a chance the bone fragments will never grow back together. In these situations, the healing that does occur would likely result in a bone that is very weak or shortened. What is needed is an apparatus which is capable of not only holding the remaining portions of the bone together, but also capable of supporting or replacing the section of the bone that is unlikely to mend, so as to provide strength and the ability to restore the bone's original length.

In addition, if the device is one which is meant to remain in the body long term, complications often occur after time due to the contact of the metal with the bone and surrounding tissues. Attempts have been made to construct the aforementioned devices of materials more compatible with the body. As a result many of the prior art devices made of exotic plastics or metals. However, the use of these materials is done at the expense of the strength.

Wherefore, it is an object of this invention to provide an apparatus capable of supporting or replacing sections of bone, thereby strengthening the bone and allowing for the accurate restoration of the bone's original length.

Wherefore, it is another object of this invention to provide an apparatus constructed of strong, resilient metals, but insulated with a material that is body-compatible so as to prevent contact between the metals and the bone and tissues of the patient.

Wherefore, it is still another object of this invention to provide an apparatus which is easy and quick to install, thereby permitting shorter surgery time.

SUMMARY OF THE INVENTION

The present invention is directed to an apparatus which resolves the above-described disadvantages of current bone fixation devices. This resolution is achieved through an internal bone fixation apparatus for supporting and securing together two sections of a fractured elongated bone within a patient's body. Generally, the apparatus includes first and second fixation portions which are disposed in holes formed in the internal cavity of the fractured bone on respective sides of the fracture, and a means for connecting these fixation portions together. In the preferred version of the present invention, the connecting means is adjustable such that the first and second fixations portions can be drawn together or spread apart in the longitudinal direction, thereby similarly moving the first and second sections of the fractured bone. This process allows a desired length of the overall elongated bone to be obtained. Consequently, for elderly patients where a fractured bone may not heal properly, and for patients where the fracture site is so severely shattered that there is little chance the bone fragments will never grow back together, the adjustable version of this invention will allow the fractured bone to be supported and supplemented as well as restored to its original length. Therefore, the object of this invention to provide an apparatus capable of supporting or replacing sections of bone, thereby strengthening the bone and allowing for the accurate restoration of the bone's original length has been achieved.

Each fixation portion of the preferred version of the present invention includes a means for securing it in the hole formed in the internal cavity of the respective sides of the fractured bone, and a means for insulating the securing means from contact with the patient's body. In one specific embodiment, each securing means includes an expansion bolt and a screw. The expansion bolt is of a generally hollow shape and open at both ends, in an unexpanded state. One end of the expansion bolt has a internally threaded section, and the other end has a flanged section. The flanged section has an outer diameter larger than the remainder of the expansion bolt. There is also a radially expandable section disposed between the internally threaded section and the flanged section which includes a plurality of longitudinal slats, the longitudinal slats being deformable to an expanded state wherein they bulge outward when a longitudinal compressive force is applied to ends of the expandable section and tightly press against any surrounding surface contacted.

The screw provides this longitudinal compressive force. It is of a generally cylindrical shape and has a flange which forms a boundary between a first threaded section on one side and the remainder of the screw on the other. The diameter of the side of the screw opposite the first threaded section is sized so that it is slidable through an inner bore of the hollow expansion bolt. The flange, however, has a larger diameter than the bore and so can not slide through. There is also a second threaded section on the end of the screw opposite the first threaded section. The second threaded section is matable with the internally threaded section of the expansion bolt.

The screw is disposed within the bore of the expansion bolt such that the second threaded section of the screw is mated with the internally threaded section of the expansion bolt and a surface of the flange of the screw is in contact with the flanged section of the expansion bolt. The expandable section is initially unexpanded prior to the securing of the fixation portion in the hole of the respective fractured bone segment. The fixation portion is secured by rotating the screw within the expansion bolt such that a compressive force is applied to the ends of the expansion section, thereby causing the longitudinal slats to bulge outward as described above.

The insulating means insulates the securing means, which is contained therein, from contact with the patient's body. The insulating means includes a housing which is of a generally hollow cylindrical shape, closed at one end and open at another, and disposed in the hole formed in the internal cavity of a respective fractured bone segment. The housing has a flanged section at the open end which has a larger outer diameter than a remainder of the housing. The back face of the flanged section abuts the end of the respective section of the fractured bone, and the remainder of the housing fits snugly in the hole formed therein. The flanged section also has an indented section at the open end thereof which has a larger diameter than the internal bore of the housing and a depth equal to the flanged section of the expansion bolt such that the flanged section of the expansion bolt is disposed completely within this indented section. The inner bore of the housing is large enough to accommodate the expansion bolt and screw combination which is disposed therein.

The insulating means is completed by the addition of a quantity of an insulating compound sufficient to completely fill all voids existing between the interior surface of the housing and the therein disposed parts of the expansion bolt and screw. The exterior surface of the housing tightly presses against the surface of the bone within the hole when the expandable section is in the expanded state after the aforementioned securing.

The connection means in the preferred version of the present invention includes an adjustment means and a means for insulating the adjustment means from contact with the patient's body. In one specific embodiment, the hole formed in the internal cavity of the second section of the fractured bone is made coaxial to the hole formed in the internal cavity of the first section of the fractured bone. In addition, the first threaded section of the screw in a first fixation portion has right-hand threads and the first threaded section of the screw in a second fixation portion has left-hand threads. The adjustment means in this version include a screw coupling having a generally hexagonal cross-section along its longitudinal length, with a central bore which includes a first internally threaded section at one end having right-hand threads which are mated with the first treaded section of the screw in the first fixation portion, and a second internally threaded section at another end having left-hand threads which are mated with the first threaded section of the screw in the second fixation portion. The adjustment is accomplished by rotating the screw coupling a first direction to draw together the first and second sections of the fractured bone, and rotated an opposite direction to spread apart.

The insulating means includes a tube having a generally hollow cylindrical shape which is open at both ends, and an inner diameter equal to the outer diameter of the flanged sections of the housings in the fixation portions. It is also of sufficient length to traverse the distance between the ends of the first section of the fractured bone and the second section of the fractured bone. The inner surface at each end of the tube contacts an outer periphery of the flanged sections of said housings, respectively, and each end face of the tube contacts the end faces of the first and second bone sections, respectively.

The insulating means is completed by a quantity of an insulating compound sufficient to completely fill all voids existing between the interior surface of the tube and the therein disposed screw coupling and first threaded sections of the screws.

The purpose for insulating the expansion bolts, screws, and screw coupling derives from the materials from which each is made. The expansion bolts, screws, and screw coupling are made of a resilient metal which has qualities not compatible for long term contact with the patient's body. These materials were chosen for their strength which facilitates their structural support and securing functions. As was stated previously, attempts have been made to construct bone fixation devices of materials which are compatible with body by the use of oexotic plastics and metals. However, the use of these materials is done at the expense of the strength. Therefore, the preferred version of the present invention makes the structural and securing portions of the fixation apparatus from strong, resilient metals, but completely isolates them from any contact with the body of the patient. The insulating materials are all compatible for long term contact with the body of the patient. Thus, the strength that the resilient metals provide is taken advantage of, while the disadvantages of their incompatibility with the body of the patient are eliminated. Accordingly, the object of this invention to provide an apparatus constructed of resilient metals, but insulated with a material that is body-compatible so as to prevent contact between the metals and the body of the patient has been achieved.

In one specific embodiment of this invention, the screws and screw coupling are made from a resilient steel, and the expansion bolts are made from steel also. The steel of the screws and screw coupling provides structural support. The steel of the expansion bolts allows the slats of the expandable section thereof to be flexible enough to deform under the compressive force exerted by the screw, but resilient enough to exert a significant force against the interior surface of the housing when the expandable section is in the expanded state.

The housing, tube, and their associated insulating compound are made of body-compatible materials suitable for long term contact. The housing is made of a plastic material and its associated insulating compound is made of a material which is initially fluid, but hardens after installation. The hardened compound not only isolates the metal parts from the patient's body, but also provides sufficient adhesion and resistive strength to prevent backing off of the slats and screws.

The tube is also made of a plastic material, and further includes a longitudinal slot along its entire length such that the tube can be installed by spreading it apart at the slot a sufficient distance to allow the tube to be placed around the connection means. The plastic material is not only body-compatible but it is flexible enough to allow the tube to be spread open at the slot, but resilient enough that the tube returns to its original shape after being released from this spreading. In addition, the interior of the tube is filled with insulating compound through the slot. The insulating compound has identical properties to that used in the fixation portions, and the hardened compound provides sufficient adhesion and resistive strength to prevent rotation of the screw coupling and movement of the first and second sections of the fractured bone relative to each other.

As can be envisioned, the fixation portions are secured and connected together with ease, and only simple adjustments are necessary in order to obtain the desired length of the restored bone. Therefore, the object of this invention to provide an apparatus which is easy and quick to install, thereby permitting shorter surgery time has also been achieved.

BRIEF DESCRIPTION OF THE DRAWINGS

These and other features, aspects, and advantages of the present invention will become better understood with regard to the following description, appended claims, and accompanying drawings where:

DETAILED DESCRIPTION OF THE INVENTION

Figure 1:
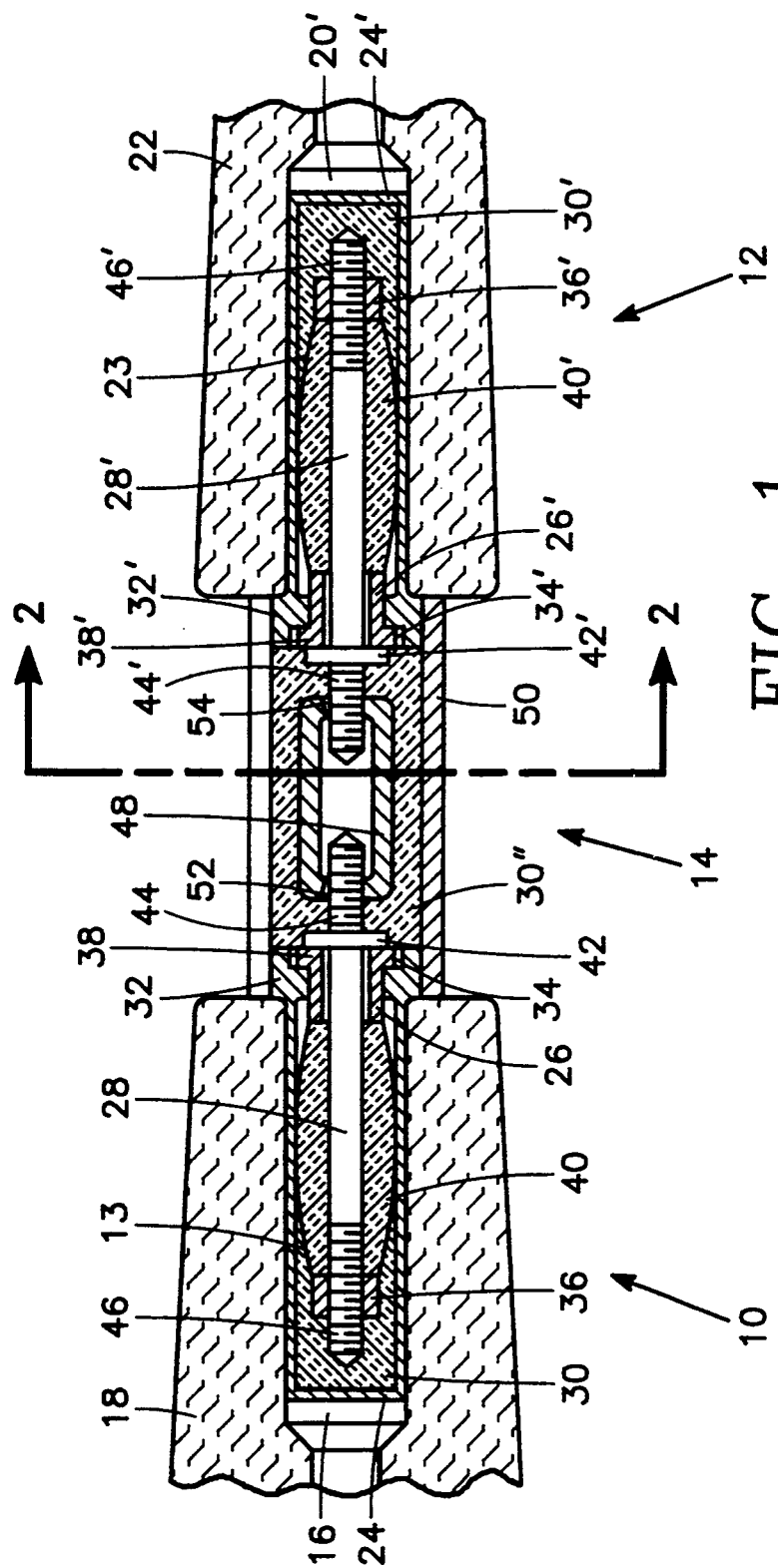
FIG. 1 is a longitudinal sectional view of the segments of an elongated bone on either side of a fracture, with the internal bone fixation apparatus of the present invention installed.
Figure 2:
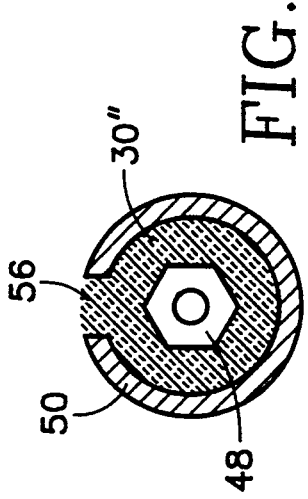
FIG. 2 is a cross-sectional view along the line A—A of FIG. 1.

A preferred version of the bone fixation apparatus in accordance with the present invention is illustrated in FIG. 1. In its most general form, the apparatus includes a top fixation portion 10, bottom fixation portion 12, and a connection portion 14. The top fixation portion is disposed in a generally cylindrical hole 16 formed in the internal cavity of the upper bone section 18. The bottom fixation portion 12 is disposed in a generally cylindrical hole 20 formed in the lower bone section 22. The top fixation portion 10 is connected to the bottom fixation portion 12 via the connection portion 14. It is noted that the diameter of the top fixation portion 12 and the bottom fixation portion 14 are dictated by the size of the elongated bone to be repaired. For example, the diameter of the fixation portions 10, 12 could be quite small if a human finger bone were being repaired. Whereas, the diameter of the fixation portion 10, 12 would be quite large if the bone to be repaired was in the leg of an elephant.

The top fixation portion 10 is comprised of a plastic housing 24, and expansion bolt 26, a screw 28, and a quantity of insulating compound 30. The plastic housing 24 is of a generally hollow cylindrical shape and closed at one end. The open end of the plastic housing 24 has a flanged section 32 which has a larger outer diameter than the remainder of the plastic housing 24. The flanged section 32 has an indented shoulder 34 at the open end which has a slightly larger diameter than the internal bore of the overall plastic housing 24. The diameter of plastic housing 24 is such that it snugly fits into the hole 16 and the length is such that it can be completely inserted into the hole 16 whereby the back shoulder of the flanged section 32 abuts the upper bone section 18. The housing 24 is made of a body-compatible plastic material, such as, but not limited to, surgical-type polyethylene.

The expansion bolt 26 in its unexpanded state is of a generally hollow shape and open at both ends. One end of the expansion bolt 26 has a internally threaded section 36. The opposite end of the bolt 26 has a flanged section 38. The flanged section 38 has a outer diameter larger than the remainder of the bolt 26 and just slightly smaller than the indented shoulder 34 of the plastic housing 24, but larger than the internal bore of the housing 24. The longitudinal length of the flanged section 38 is such that it completely fits into the confines of the indented shoulder 34. An radially expandable section 40 is disposed between the threaded section 36 and the flanged section 38 of the bolt 26. The expandable section 40 is comprised of a plurality of longitudinal slats. The slats are deformable to an expanded state wherein they bulge outward when a longitudinal compressive force is applied to the ends of the expandable section 40. Although deformable, the slats are also resilient enough to apply a considerable outward force against the surface of the internal bore of the plastic housing 24 when in the expanded state. The diameter and length of the expandable section 40 in its unexpanded state together with the threaded portion 36, is such that the overall diameter is slightly smaller and the length is approximately one-fifth shorter than the internal bore of housing 24. The expansion bolt 26 is preferable made of a resilient, hardened steel. These materials will provide the aforementioned resiliency and deformability attributes.

The screw 28 is of a generally cylindrical shape and threaded at both ends. There is a flange 42 which forms the boundary between a first threaded section 44 on one end of the screw 28 and the remainder of the screw 28. The diameter of the screw 28 is sized so that it is slidable through the inner bore of the expansion bolt 26 from the flanged end of the bolt 26, except a second threaded section 46 on the opposite end of the screw 28 from the first threaded section 44 is additionally sized to interface with the internally threaded section 36 of the expansion bolt 26 and be of the same thread type. The flange 42 has a diameter larger than the remainder of the screw 28, and is further sized to be larger than the inner bore of the expansion bolt 26, but smaller than flanged section 38 of the bolt 26. The length of the portion of the screw 28 beyond the flange 42 and opposite the first threaded section is just slightly shorter than the length of the internal bore of the plastic housing 24. The second threaded section 46 covers approximately one-third of the that length. The threads on the first threaded section 44 are right-handed, and extend from the end of screw 28 to the flange 42, a distance approximately equal to the length of the second threaded section 46. The screw 28 is preferably made from a resilient, hardened steel.

The insulating compound 30 is a material which is compatible with the body of a patient and appropriate for long term contact with the bone and surrounding tissues thereof. The compound 30 is initially fluid, but hardens after installation. After hardening, the compound 30 provides sufficient adhesion and resistive strength to prevent the movement of any of the other components within the top fixation portion 10, in relation to each other. An example of an appropriate compound 30 is a acrylic dental cement, such as that sold under the mark, "Simplex Rapid". However, this is not meant to limit the present invention in regards to the insulating compound 30 by virtue of the disclosure of a specific example thereof. The compound 30 can be any material with the aforementioned qualities.

The top fixation portion is installed in the following way. First, the surgeon forms the appropriate size hole 16 in the medullar cavity of the upper bone section 18. Next, the surgeon pours the insulating compound 30, in its initial fluid state, into the open end of plastic housing 24. The screw 28 is inserted into the inner bore of the expansion bolt 26, such that the end with the second treaded section 46 is inserted first. When the second threaded section 46 contacts the internally threaded section 36 of the expansion bolt 26, the screw 28 is rotated until the flange 42 of the screw 28 just contacts the flange 38 of the bolt 26, ensuring the expansion section 40 remains in its non-expanded state. The expansion bolt 26 and screw 28 are then inserted into the open end of housing 24, such that end with the protruding second threaded portion 46 is inserted first and the rear face of the flanged section 38 is seated against the back of the indented shoulder 34 of the plastic housing 24. The now completely assembled top fixation portion 10 is inserted into hole 16 in the upper bone section 18, such that the closed end of the plastic housing 24 is inserted first, and the rear shoulder of the flange section 32 is seated against the end of the bone 18. When the top fixation section 10 is properly seated in the bone 18, but before the insulating compound 30 has hardened, the screw 28 is rotated so as to cause the expandable section 40 of the expansion bolt 26 to bulge and contact the surface of the internal bore of the plastic housing 24. Once contact is made, the screw 28 is further rotated to until the exterior surface of the plastic housing 24 tightly presses against the surface of the bone 18 within the hole 16 formed therein. After the insulating compound 30 has hardened, the expandable section 40 become locked into the expanded position, thereby preventing the top fixation portion 10 from being dislodged. It should also be mentioned that only the body-compatible plastic material of the housing 24 is making contact with the bone 18, none of the metal components are in contact.

The bottom fixation portion 12 is configured almost identical to the top fixation portion 10. Like numbers have been used in FIG. 1 to identify like components making up the bottom fixation portion 12, however a prime mark has been added for differentiation purposes. The only difference between the configuration of the top fixation portion 10 and the bottom fixation portion 12 is that the first threaded portion 44' on the screw 28' in the bottom fixation portion 12 has left-handed threads instead of right-handed threads. The installation process to insert the bottom fixation portion 12 into the lower bone section 22 is identical to that described in connection with the top fixation portion 10 and the upper bone section 18. The only additional step is that the hole 20 formed in the lower bone section 22 is made to be coaxial with the hole 16 in the upper bone section 18, in the longitudinal direction.

The connection portion 14 is comprised of a screw coupling 48, a longitudinally slotted plastic tube 50, and a quantity of insulating compound 30". The screw coupling 48 has a generally hexagonal cross-section along its longitudinal length, with a central bore which is internally threaded at each end. The first internally threaded section 52 has right-hand threads and is sized to mate with the threaded section 44 of screw 28 in the top fixation portion 10. The second internally threaded section has left-hand threads and is sized to mate with the threaded section 44' of screw 28' in the bottom fixation portion 12. The screw coupling is made of a hardened steel.

The plastic tube 50 is of a generally hollow cylindrical shape, except it has a slot 56 which runs longitudinally from one end to the other. The tube 50 has an inner diameter equal to the outer diameter of the flanged sections 32, 32' of the plastic housings 24, 24' in the top and bottom fixation sections 10, 12. The tube 50 is also of sufficient length to traverse the distance between the ends of the upper bone section 18 and the lower bone section 22, after the below described installation. The tube 50 is made of a body-compatible plastic material which is flexible enough to allow the tube 50 to be spread open from the slot 56, but resilient enough to return to its original shape after such speading. The plastic material can be, but not limited to, surgical polyethylene.

The insulating compound 30" has the same properties as the insulating compound 30, 30' used in the top and bottom fixation portions 10, 12. It can be the same material if desired.

The connection portion 14 is used to connect the top fixation portion 10 to the bottom fixation portion 12, thereby connecting the two sections of the fractured bone being restored. To accomplish this connection, the first threaded section 52 of the screw coupling 48 is installed onto the first threaded section 44 of the screw 28 in the top fixation portion 10. The second threaded section 54 of the screw coupling 48 is then similarly installed on the first threaded section 44' of the screw 28' in the bottom fixation portion 12. Once installed, the surgeon rotates the screw coupling in a first direction to draw the top and bottom fixation portions 10, 12 together, and in the opposite direction to spread the fixation portions 10, 12 apart, such that the desired separation of the bone sections 18, 22 of the fractured bone is obtained. Typically, the desired separation would effectively restore the bone to its original length. This procedure is possible because of the right-hand thread configuration of the first threaded section 52 of the screw coupling 48 in conjunction with the right-hand threads of the first threaded section 44 of the screw 28 in the top fixation section 10, and the left-hand thread configurations of the corresponding second threaded section 54 of the screw coupling 48 in conjunction with the first threaded section 44' of screw 28' in the bottom fixation portion 12.

Once the above mentioned separation is obtained, the surgeon installs the plastic tube 50. The plastic tube 50 is installed by spreading it apart at the slot enough to allow it to be placed around the screw coupling 48 and into contact with the flanged sections 32, 32' of the plastic housings 24, 24' in the top and bottom fixation portions 10, 12. This contact is such that the inner surface at the ends of the plastic tube 50 touch the outer periphery of the flanged sections 32, 32'. In addition, the end faces of the tube 50 are in contact with the ends of the upper and lower bones sections 18, 22, respectively.

The surgeon next fills the interior of the tube 50 with insulating compound 30" through its slot 56 to complete the installation process. After the insulating compound 30" has hardened, the screw coupling 48 and the top and bottom fixation portions 10, 12 are fixed in place and no movement between the parts is possible. In addition, only the body-compatible plastic material of the housing 24 and the insulating compound 30" is making contact with the patient's body, none of the metal components are in contact.

Although the present invention has been described in considerable detail with reference to certain versions thereof, other versions are possible. Therefore, the spirit and scope of the appended claims should not be limited to the description of the versions of this invention contained herein.

I claim:

1. An internal bone fixation apparatus for supporting and securing together two sections of a fractured elongated bone within a patient's body, the apparatus comprising:

a) a first fixation portion disposed in a hole formed in the internal cavity of a first section of the fractured bone on one side of the fracture wherein the first fixation portion includes a first means for securing the first fixation portion in the hole formed in the internal cavity of the first section of the fractured bone, and a first means for insulating the securing means from contact with the patient's body, and wherein the first securing means comprises:

a1) an expansion bolt which is of a generally hollow shape and open at both ends, in an unexpanded state, wherein a first end of the expansion bolt has a internally threaded section, and a second end has a flanged section having an outer diameter larger than the remainder of the expansion bolt, and a radially expandable section is disposed between the internally threaded section and the flanged section which includes a plurality of longitudinal slats, the longitudinal slats being deformable to an expanded state wherein they bulge outward when a longitudinal compressive force is applied to ends of the expandable section and tightly presses against a surrounding surface contacted, and, a2) a screw which is of a generally cylindrical shape and has a flange which forms a boundary between a first threaded section on a first end of the screw and the remainder of the screw, and wherein the diameter of the remainder of the screw is sized so that it is slidable through an inner bore of the hollow expansion bolt, whereas the flange is larger than the bore and not slideable therethrough, and wherein the screw has a second threaded section on a second end opposite the flange, the second threaded section matable with the internally threaded section of the expansion bolt, and wherein, a3) the screw is disposed within the bore of the expansion bolt such that the second threaded section of the screw is mated with the internally threaded section of the expansion bolt and a surface of the flange of the screw is in contact with the flanged section of the expansion bolt, and the expandable section is in one of (i) the unexpanded state prior to the securing of the first fixation portion in the hole formed in the internal cavity of the first section of the fractured bone, and (ii) the expanded state after such securing, the securing being accomplished by rotating the screw within the expansion bolt such that a compressive force is applied to the ends of the expansion section;

b) a second fixation portion disposed in a hole formed in the internal cavity of a second section of the fractured bone on the opposite side of the fracture from the first section of the fractured bone wherein the second fixation portion includes a second means for securing the second fixation portion in the hole formed in the internal cavity of the second section of the fractured bone, and a second means for insulating the securing means from contact with the patient's body, and wherein the second securing means is identical to the first securing means; and c) a means for connecting the first fixation portion to the second fixation portion wherein the connecting means is adjustable such that the first and second fixations portions can be one of (i) drawn together, and (ii) spread apart in a longitudinal direction, thereby similarly moving the first and second sections of the fractured bone so that a desired length of the overall elongated bone can be obtained.

2. The bone fixation apparatus of claim 1 wherein:

a) the screws in each of said fixation portions are made of a resilient steel which has qualities not compatible for long term contact with the patient's body;

b) the expansion bolts in each of said fixation portions is made of a steel not compatible for long term contact with the patient's body, and wherein the longitudinal slats of the expandable section thereof are flexible enough to deform under the compressive force exerted by the screw, but resilient enough to exert a significant force against the surrounding surface contacted when the expandable section is in the expanded state.

3. The bone fixation apparatus of claim 1 wherein:

a) the first means for insulating the first securing means from contact with the patient's body wherein the first securing means is contained completely within the first insulating means, the first insulating means comprising:

a1) a housing which is of a generally hollow cylindrical shape, closed at one end and open at another, and disposed in the hole formed in the internal cavity of the first section of the fractured bone, and wherein a flanged section exists at the open end which has a larger outer diameter than a remainder of the housing such that a back face of the flanged section of the housing abuts an end of said section of the fractured bone and the outer diameter of the remainder of the housing is such that it is snugly disposed in the hole formed in said internal cavity and the inner diameter is larger than the securing means contained completely therein, and, a2) a quantity of an insulating compound sufficient to completely fill all voids existing between the interior surface of the housing and the therein disposed securing means, and wherein, a3) the exterior surface of the housing is tightly pressed against the surface of the bone within said hole by the securing means; and, b) the second means for insulating the second securing means from contact with the patient's body wherein the second securing means is contained completely within the second insulating means, the second insulating means being identical to the first insulating means.

4. The bone fixation apparatus of claim 3 wherein:

a) the housing is made of a plastic material compatible for long term contact with the patient's body; and, b) the insulating compound comprises a material which is compatible for long term contact with the patient's body, and which is initially fluid, but hardens after installation, the hardened compound providing sufficient adhesion and resistive strength to prevent release of the securing means.

5. The bone fixation apparatus of claim 4 wherein the hole formed in the intramedullary cavity of the second section of the fractured bone is made coaxial to the hole formed in the intramedullary cavity of the first section of the fractured bone.

6. The bone fixation apparatus of claim 5 wherein the first fixation portion includes a screw protruding from the center of the hole formed in the first section of the fractured bone and having right-hand threads, and wherein the second fixation portion includes a screw protruding from the center of the hole formed in the second section of the fractured bone and having left-hand threads, and wherein further, the adjustment means comprises:
   a) a screw coupling having a generally hexagonal cross-section along its longitudinal length, with a central bore which includes a first internally threaded section at one end having right-hand threads which are mated with the screw in the first fixation portion and a second internally threaded section at another end having left-hand threads which are mated with the screw in the second fixation portion, wherein said adjustment is accomplished by rotating the screw coupling a first direction to draw together the first and second sections of the fractured bone, and rotated an opposite direction to spread apart the first and second sections of the fractured bone.

7. The bone fixation apparatus of claim 1 wherein:
   a) the first means for insulating the first securing means from contact with the patient's body wherein the first securing means is disposed within the first insulating means, the first insulating means comprising:
      a1) a housing which is of a generally hollow cylindrical shape, closed at one end and open at another and disposed in the hole formed in the internal cavity of the first section of the fractured bone, and wherein a flanged section exists at the open end which has a larger outer diameter than a remainder of the housing and includes an indented section at the open end thereof which has a larger diameter than an internal bore of the housing and a depth equal to the flanged section of the expansion bolt such that said flanged section of the expansion bolt is disposed completely within the indented section and a back face of the flanged section of the housing abuts an end of said section of the fractured bone, and wherein, the outer diameter of the remainder of the housing is such that it is snugly disposed in the hole formed in said internal cavity and the inner diameter is larger than said remainder of the expansion bolt which is disposed therein and the interior length is such than the length of said remainder of the screw is contained completely therein, and,
      a2) a quantity of an insulating compound sufficient to completely fill all voids existing between the interior surface of the housing and the therein disposed remainders of the expansion bolt and screw, when the expandable section of the expansion bolt is in its expanded state, and wherein,
      a3) the exterior surface of the housing tightly presses against the surface of the bone within said hole when the expandable section is in the expanded state after said securing; and,
   b) the second means for insulating the second securing means from contact with the patient's body wherein the second securing means is disposed within the second insulating means, the second insulating means being identical to the first insulating means.

8. The bone fixation apparatus of claim 7 wherein the connection means comprises:
   a) a means for adjustment; and
   b) a third means for insulating the adjustment means from contact with the patient's body.

9. The bone fixation apparatus of claim 8 wherein the hole formed in the internal cavity of the second section of the fractured bone is made coaxial to the hole formed in the internal cavity of the first section of the fractured bone.

10. The bone fixation apparatus of claim 9 wherein the first threaded section of the screw in the first fixation portion has right-hand threads and the first threaded section of the screw in the second fixation portion has left-hand threads, and wherein further, the adjustment means comprises:
   a) a screw coupling having a generally hexagonal cross-section along its longitudinal length, with a central bore which includes a first internally threaded section at one end having right-hand threads which are mated with the first treaded section of the screw in the first fixation portion and a second internally threaded section at another end having left-hand threads which are mated with the first threaded section of the screw in the second fixation portion, wherein said adjustment is accomplished by rotating the screw coupling a first direction to draw together the first and second sections of the fractured bone, and rotated an opposite direction to spread apart said first and second sections of the fractured bone.

11. The bone fixation apparatus of claim 10 wherein the third insulating means comprises:
   a) a tube having a generally hollow cylindrical shape which is open at both ends, and wherein the tube has an inner diameter equal to the outer diameter of the flanged sections of the housings in the first and second fixation portions and sufficient length to traverse the distance between the ends of the first section of the fractured bone and the second section of the fractured bone, and wherein further, an inner surface at each end of the tube contacts an outer periphery of the flanged sections of said housings, respectively, and each end face of the tube contacts the end faces of the first and second bone sections, respectively; and
   b) a quantity of an insulating compound sufficient to completely fill all voids existing between the interior surface of the tube and the therein disposed screw coupling and first threaded sections of the screws of said first and second fixation portions.

12. The bone fixation apparatus of claim 11 wherein:
   a) the screws in each of said fixation portions and the screw coupling are made of a resilient steel which has qualities not compatible for long term contact with the patient's body;
   b) the expansion bolts in each of said fixation portions is made of a steel not compatible for long term contact with the patient's body, and wherein the slats of the expandable section thereof are flexible enough to deform under the compressive force exerted by the screw, but resilient enough to exert a significant force against the interior surface of the housing when the expandable section is in the expanded state;
   c) the housing is made of a plastic material compatible for long term contact with the patient's body;
   d) the insulating compound used in the top and bottom fixation portions comprises a material which is compatible for long term contact with the patient's body, and which is initially fluid, but hardens after installation, the hardened compound providing sufficient adhesion and resistive strength to prevent backing off of the slats and screws;

e) the insulating compound used in the connection portion comprises a material which is compatible for long term contact with the patient's body, and which is initially fluid, but hardens after installation, the hardened compound providing sufficient adhesion and resistive strength to prevent rotation of the screw coupling and movement of the first and second sections of the fractured bone relative to each other; and, f) the tube further includes a longitudinal slot along its entire length such that the tube can be installed by spreading it apart at the slot a sufficient distance to allow the tube to be placed around the screw coupling and first threaded sections of the screws of said first and second fixation portions and in contact with the flanged sections of said housings and said sections of the fractured bone, and wherein the tube is made of a plastic material compatible for long term contact with the patient's body which is flexible enough to allow the tube to be spread open at the slot, but resilient enough that the tube returns to its original shape after being released from spreading, and wherein the interior of the tube is filled with insulating compound through the slot.

* * * * *